United States Patent [19]
Morse et al.

[11] Patent Number: 5,984,937
[45] Date of Patent: *Nov. 16, 1999

[54] ORBITAL DISSECTION CANNULA AND METHOD

[75] Inventors: Stephen A. Morse, Palo Alto; Peter L. Callas, Redwood City; Geoffrey A. Orth, Windsor; Andrew G. C. Frazier, Rewood City; Albert K. Chin, Palo Alto, all of Calif.

[73] Assignee: Origin Medsystems, Inc., Menlo Park, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/828,578

[22] Filed: Mar. 31, 1997

[51] Int. Cl.⁶ .................................................. A61B 17/00
[52] U.S. Cl. .............................. 606/170; 604/22; 606/45; 606/180
[58] Field of Search ................................. 606/1, 159, 170, 606/171, 180, 45; 604/22

[56] References Cited

U.S. PATENT DOCUMENTS

| | | | |
|---|---|---|---|
| 5,498,258 | 3/1996 | Hakky et al. | 606/170 |
| 5,527,331 | 6/1996 | Kresch et al. | 604/22 |
| 5,591,183 | 1/1997 | Chin | 606/159 |
| 5,601,581 | 2/1997 | Fogarty et al. | |
| 5,658,282 | 8/1997 | Daw et al. | 606/159 |

*Primary Examiner*—Michael Buiz
*Assistant Examiner*—William Lewis
*Attorney, Agent, or Firm*—Fenwick & West LLP

[57] ABSTRACT

A cannula and method provide manually manipulable orientation of a dissection probe carried eccentricity on the cannula for rotational and translational positioning relative to the field of view of an endoscope at a distal end of the cannula. Rotation of the cannula at fixed axial position relative to the endoscope, and rotational and translational positioning of the dissection probe relative to the distal end of the cannula provide wide-area access within the surgical site for bluntly dissecting connective tissue surrounding a vessel of interest being harvested.

14 Claims, 3 Drawing Sheets

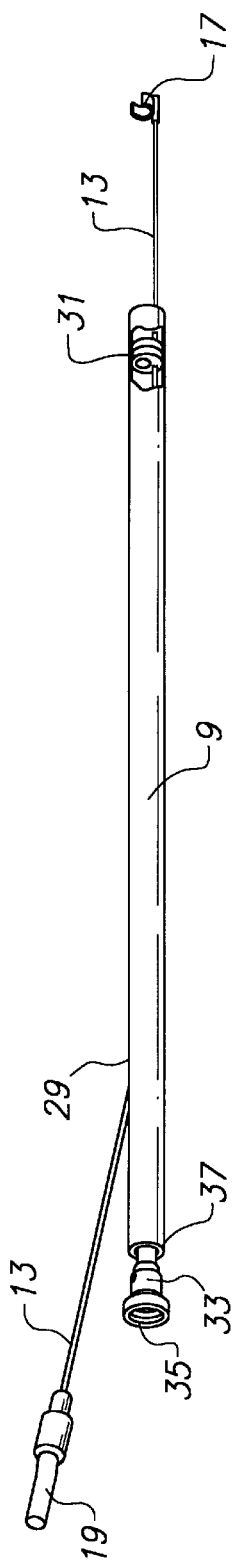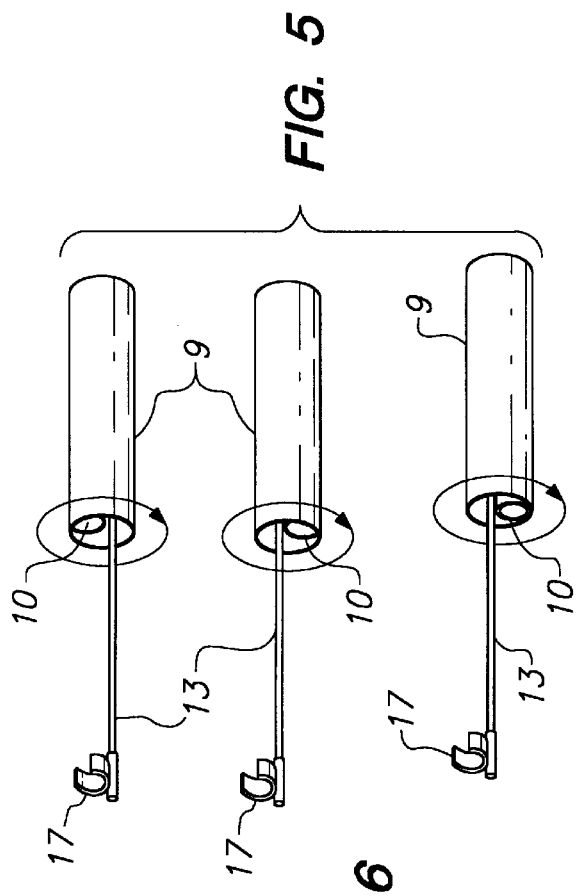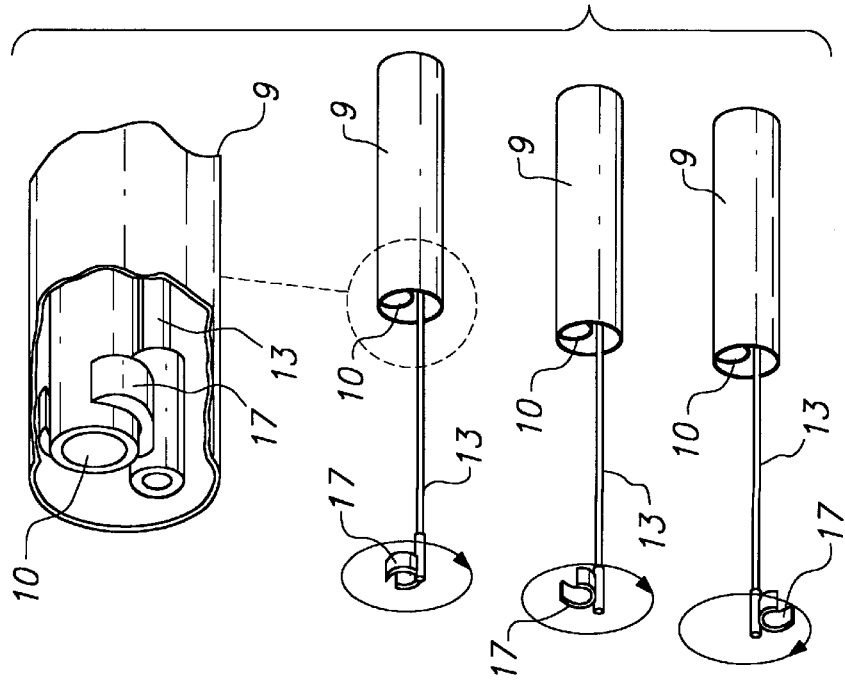

ORBITAL DISSECTION CANNULA AND METHOD

FIELD OF THE INVENTION

This invention relates to a multiple lumen cannula, and more particularly to a cannula and method that includes an endoscope disposed within one lumen toward a distal end, and that includes a ringed dissection probe disposed for axial and rotational movement within a second lumen for use, for example, within an insufflated surgical cavity during harvesting of a vessel of interest.

BACKGROUND OF THE INVENTION

Certain known dissection devices include a ring or hook attached to a shaft that extends axially for operation as a dissection tool. Such dissection tools engage a vessel to be dissected, e.g., the saphenous vein, and are pushed and pulled to separate the vessel from surrounding connecting tissue. Devices of these types are disclosed in the literature (see, for example, U.S. Pat. Nos. 5,591,183 and 5,601,581).

Such devices commonly looped around a vessel during its dissection within narrow confines of a small working cavity about the vein. As vessel branches and tributaries are encountered, the ring or loop may have to be removed from the working cavity and reintroduced at a position on the other side of the branch or tributary in order to avoid avulsing such side branches. Since a harvested vessel such as the saphenous vein will be required to withstand arterial pressure without leakage (e.g., in coronary artery bypass surgery), such side branches or tributaries are ligated with sutures or vascular clips to prevent leakage. If avulsion of a side branch occurs close to the surface of the harvested vessel, the resultant defect in the harvested vessel must be repaired, typically with multiple stitches of fine suture. Such repair is tedious and the suture repair may decrease lumen size of the bypass, leading to premature occlusion.

Manipulating such known ring and hook type dissection probes about a vessel of interest is made more difficult by the limited space available within a working cavity at the surgical site. Although the ring or hook may be lifted to disengage from the vessel, if the vessel lies near a margin or boundary of the working cavity then insufficient space may be available to enable the ring or hook to be disengaged from the vessel. Continued effort to disengage the dissection ring may lead to side branch avulsion or injury to the vessel of interest attributable to lacerations and excessive stretching.

SUMMARY OF THE INVENTION

In accordance with the present invention, a cannula having an endoscope within one lumen may be rotated relative to the endoscope, and a dissection probe supported in another lumen of the cannula may be rotated and axially manipulated relative to the cannula substantially about an elongated axis that is eccentric to the endoscope. The endoscope may be axially fixed relative to the distal end of the cannula (and slightly recessed therefrom), and the ring-like dissection probe is disposed on an axially-extending control rod that is positioned eccentric to the endoscope. The distal end of the cannula includes a recess within which the viewing end of the endoscope may positioned to avoid smudging of the lens during advancement of the cannula through fatty connective tissue. In addition, the ring-like dissection probe may be withdrawn into the recess at the distal end of the cannula, into co-axial alignment about the endoscope and out of its field of view. Also, edges of the recess at the distal end of the cannula are arranged to be outside the viewing angle of the endoscope so that such distal edges of the cannula are not visible within the field of view of the endoscope. Gas seals are disposed around the endoscope and the control rod in order to facilitate manipulating the cannula assembly, or portions thereof, in a pressurized, insufflated working cavity at the surgical site.

DESCRIPTION OF THE DRAWINGS

FIG. 3 is a perspective view of the cannula of the present invention according to another embodiment showing a cutaway view near the distal end;

FIG. 5 is a compilation of perspective views of a partial cannula according to the present invention illustrating continuous orbital orientations of the cannula and the control rod for the dissection probe about the axis of the endoscope;

FIG. 6 is a compilation of perspective views of a partial cannula near the distal end thereof, with an inset cutaway view showing retracted orientation of the endoscope and dissection probe;

DETAILED DESCRIPTION OF THE INVENTION

Figure 1:
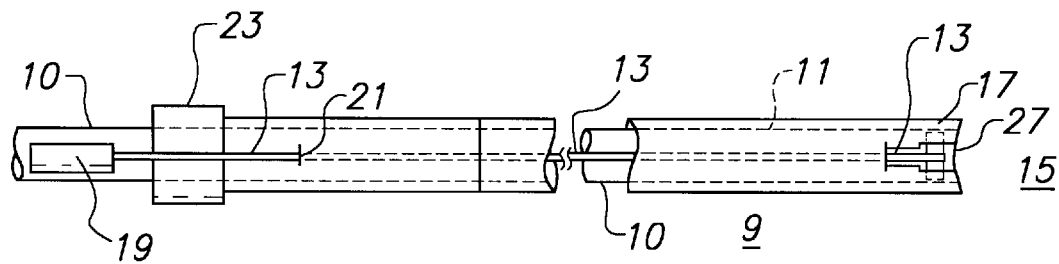
FIG. 1 is a partial top view of one embodiment of the generally cylindrical cannula according to the present invention.

Referring now to the illustrated embodiment of FIG. 1, there is shown a partial side view of the cannula 9 including a generally cylindrical outer housing 11 of bioinert material such as polycarbonate that may be approximately 12"–18" in length and of sufficient diameter to contain therein an endoscope of about 5 millimeters diameter. One major interior lumen receives an endoscope 10 therein along the length of the cannula, and another minor lumen receives the control rod 13 along substantially the entire length of the cannula 9. Near the distal end 15 of the cannula 9, the control rod 13 has attached thereto a slotted ring-like dissection probe 17 (as more fully disclosed later herein). A handle 19 for convenient finger gripping of the control rod 13 is attached at the proximal end of the control rod 13 which protrudes 21 from the side of the cannula 9 near the proximal end thereof. A sliding gas seal 23 may be disposed about the endoscope 10 for sealing against gas under pressure as the endoscope 10 is rotated and translated along the axis of the major lumen within cannula 9. The small diameter control rod 13 and close-fitting lumen in which the rod 13 slides and translates may provide adequate seal against significant leakage of gas under pressure.

Figure 2:
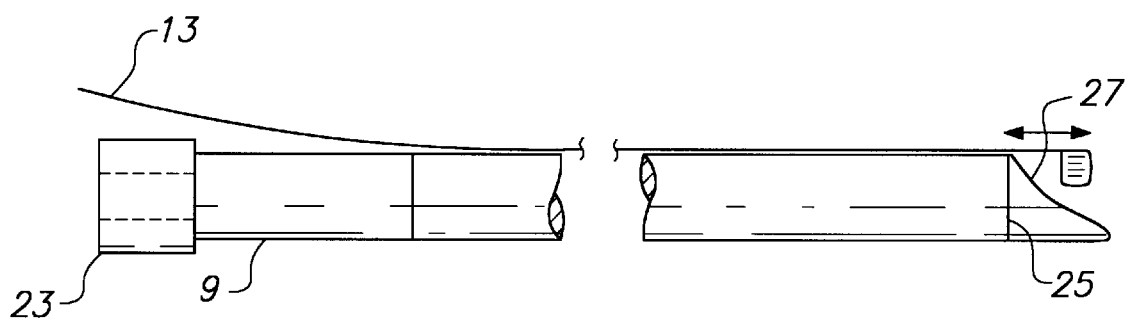
FIG. 2 is a partial side view of the embodiment of the cannula of FIG. 1 according to the present invention.

As shown in the partial side view of FIG. 2, the control rod 13 may be retained within an outer groove in the cannula 9, for example, by a heat-shrinkable sleeve or sheath 25 of bioinert material to facilitate axial and rotational positioning of the dissection probe 17. Also, to facilitate withdrawal of the dissection probe 17 from within the field of view of the endoscope 10, the perimeter of the distal edges of the cannula 9 may be slotted 27 or otherwise contoured to accommodate retraction of the dissection ring 17 attached to the control rod 13 to pull the attached ring-like dissection probe 17 to a retracted position interior of the viewing end of the endoscope 10. The distal edges of the cannula 9 may optionally be contoured or shaped suitably to facilitate blunt tissue dissection, as needed to advance the cannula into connective tissue.

Referring now to the perspective view of FIG. 3, there is shown an embodiment of the cannula 9 having a control rod 13 and attached ring-like dissection probe 17 protruding from the distal end of the cannula, as more fully described with reference to FIG. 4. In this illustrated embodiment, the control rod 13 with attached fingering handle 19 passes through the side wall 29 of the cannula 9, extends along the inner lumen of the cannula 9, and passes through gas (or other fluid) seal 31 that is recessed from the distal end of the cannula 9. In this embodiment, both the control rod 13 and an endoscope (not shown) extend along the inner lumen of the cannula and through the sliding gas seal 31 to facilitate operation of the assembly within insufflated surgical sites.

The endoscope (not shown) may attach to the collar 33 at the proximal end of the cannula 9 via mating threads 35 to fix the endoscope axially relative to the distal end of the cannula 9. Collar 33 may be rotatably attached 37 to the cannula 9 to permit rotation of the cannula 9 about the endoscope supported therein at fixed axial position of the viewing end thereof beyond the gas seal 31, but recessed from the distal edges of cannula 9 sufficiently to avoid visualizing the distal edges of the cannula 9 within the field of view of the endoscope. Thus, the passage of control rod 13 through the side wall 29 of the cannula, and the rotational mount of the collar 33 to the cannula 9 do not require gas-tight seals or fittings since the seal 31 near the distal end provides the requisite gas-tight sealing engagement between the cannula 9 and an endoscope and the control rod 13.

Figure 4:
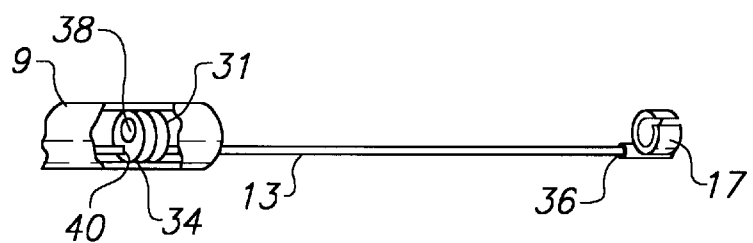
FIG. 4 is an enlarged perspective view of the distal end of the cannula showing the cutaway portion of the embodiment of FIG. 3 in greater detail.

Referring to the cut-away perspective view of FIG. 4 of the embodiment of FIG. 3, there is shown the gas seal 31 positioned recessed from the distal end of the cannula 9, with one or more laminates 34 of gasket material such as silicone rubber shaped to accommodate an endoscope, typically of about 5 millimeters diameter, in one port 38, and the control rod 13, typically of about 1–2 millimeters, in another port 40. The viewing end of an endoscope may therefore be positioned beyond the gas seal 31, but recessed from the distal edges of the cannula 9, and the ring-like dissection probe 17 may be retracted into coaxial over-lay of the viewing end of the endoscope within the recess at the distal end. Such retracted position is convenient while moving the distal end of the cannula 9 and greatly reduces the likelihood of the dissection probe 17 unintentionally engaging surrounding tissue. The dissection probe 17 may be formed of bioinert material such as polycarbonate or stainless steel for suitable attachment 36 to the control rod 13.

Figure 7A:
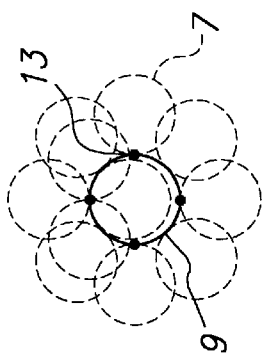
FIGS. 7A and 7B are end views of the distal end of the cannula showing various relative orientations of the ring-like dissection probe relative to the viewing axis of the endoscope.

Referring now to FIG. 5, there is shown a compilation of partial views of the distal end of the cannula 9 illustrating the viewing end of endoscope 10 recessed or retracted inwardly from the distal edges of the cannula 9. The inward retraction of the viewing end need only be to a depth at which the distal edges of the cannula 9 are not within the field of view of the endoscope 10. In addition, the endoscope 10 is shown in relatively fixed position, with the cannula 9, the control rod 13 and associated dissection probe 17 shown at various rotational positions about the endoscope 10. Similarly, as shown in the compilation of partial perspective views of FIG. 6, the control rod 13 may be rotated and axially positioned relative to cannula 9 and endoscope 10 (shown in relatively fixed positions). In addition, the dissection probe 17 is shown in the inset view as fully retracted within the recess at the distal end of the cannula 9, and positioned inwardly of the viewing end 10 of the endoscope about which the dissection probe 17 is oriented. This greatly facilitates movement of the distal end of the cannula 9 with reduced likelihood of the dissection probe 17 entangling or otherwise impairing adjacent tissue. As illustrated in the end view of FIG. 7A, the extent of 'reach' of the dissection probe 17 rotatable about the axis of control rod 13 positioned near the periphery of the cannula 9 in fixed position can be greatly increased, as shown in the end view of FIG. 7B, by also rotating the cannula 9 relative to an endoscope therewithin.

Figure 7B:
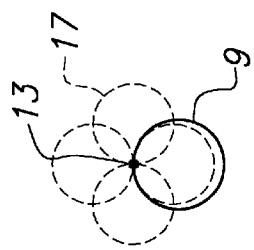
Figure 8:
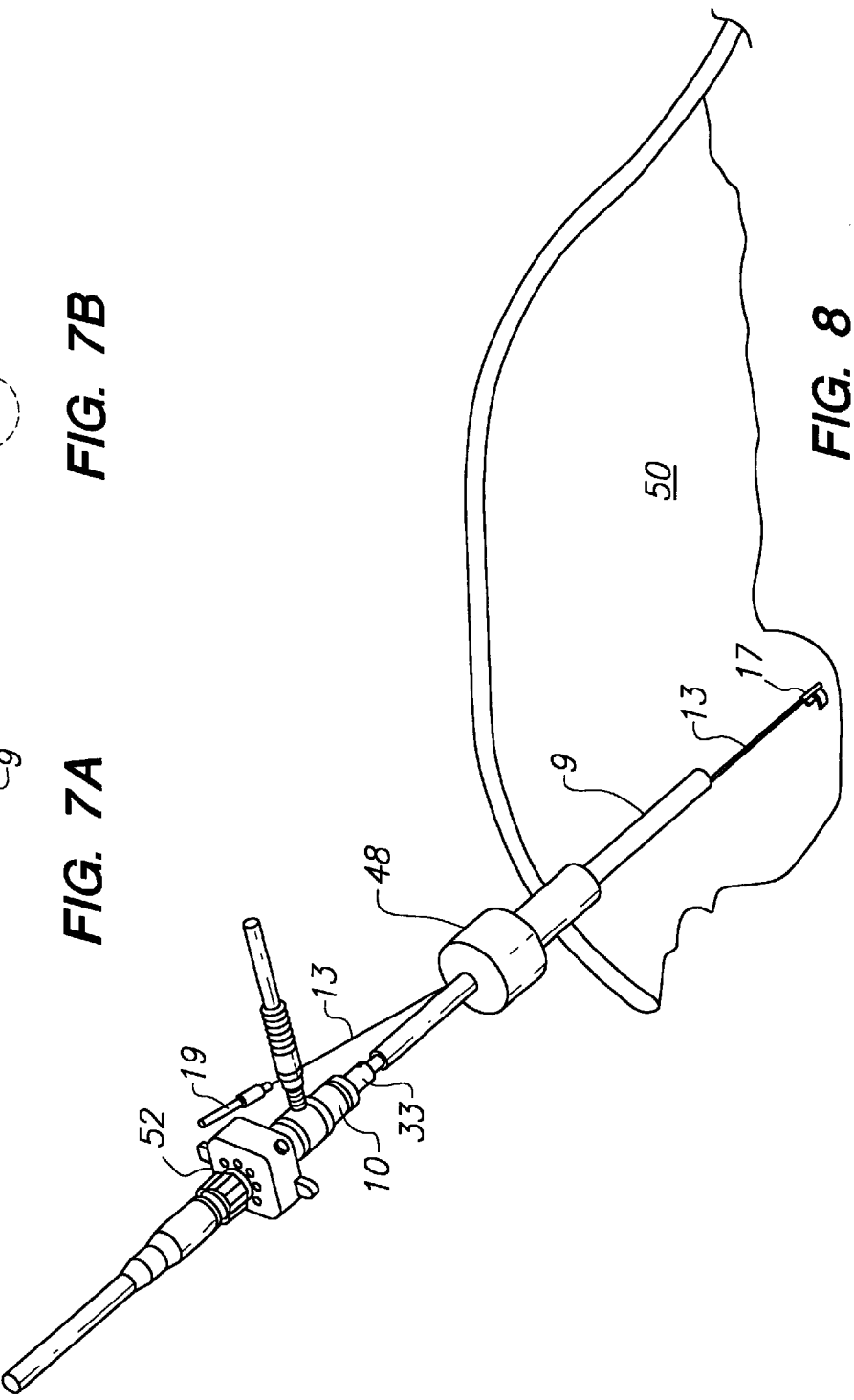
FIG. 8 is a pictorial view of the cannula of the present invention in operation within an insufflated surgical cavity.

Referring now to the pictorial view of FIG. 8, there is shown an insufflated surgical site 50 into which the cannula 9 is inserted via a gas-tight port 48 of conventional design. The control rod 13 for manipulating the dissection probe 17 is shown in place through the side wall of the cannula 9, with the fingering handle 19 disposed on the control rod 13 near the proximal end thereof to facilitate rotational and axial or translational manipulation of the dissection probe 17 over a wide area, as illustrated in FIG. 7B, relative to the location of the distal end of the cannula 9 within the insufflated surgical cavity 50. An endoscopic camera 52 may be attached to the endoscope 10 which is supported in collar 33 for fixed axial, but freely rotational, orientation within cannula 9. Thus, the cannula 9 with control rod 13 may be rotated about the endoscope 10 retained in fixed relative position, and the control rod 13 may be manipulated rotationally and axially relative to the cannula 9 in order to provide the 'reach' of covered area, as shown in FIG. 7B, relative to the distal end of the cannula 9. Alternatively, other rod-like or shaft-like instruments 13 including an endoscope may be received within the lumen in or near the side wall of the cannula for relative orbital rotation with the cannula 9 about the endscope 10.

For a surgical procedure at an insufflated surgical site, or within other surgical working cavities, the cannula 9 may be fitted with an endoscope (and camera, optionally) for freely rotatable but fixed axial positioning relative to the cannula 9. In addition, the dissection probe 17 may be configured about the viewing end of the endoscope, and be retracted within the recess at the distal end of the cannula 9. In this configuration, the cannula assembly may be inserted into the working cavity at the surgical site, and the cannula may be rotated about the endoscope. The eccentricity-oriented control rod 13 supporting the dissection probe 17 relative to the cannula 9 (or other rod-like or shaft-like instrument including an endoscope thus supported) can be positioned over an area as shown in FIG. 7B, without repositioning the distal end of the cannula 9. In addition, the control rod 13 can be manually rotated and translated relative to the cannula 9 and relative to the viewing end of the endoscope near the distal end of the cannula, for example, to facilitate tissue dissection of connective tissue from a vessel of interest to be harvested. The dissection probe 17 may then be retracted into the recess in the distal end of the cannula 9, and positioned about the viewing end of the endoscope, to facilitate convenient movement of the distal end of the cannula within the surgical site with reduced likelihood of the dissection probe entangling surrounding tissue or vessels. This configuration of the cannula (i.e., with dissection probe retracted and positioned about the viewing end of the endoscope) also greatly facilitates insertion and removal and repositioning of the cannula relative to the surgical site.

What is claimed is:

1. Surgical apparatus comprising:

an elongated cannula having distal and proximal ends and including a lumen therein between ends for receiving an endoscope in rotatable orientation therein for supporting rotation of the cannula about an endoscope disposed within said lumen; and an elongated control rod rotatably and translationally supported by the cannula eccentric of said lumen, with a dissection probe positioned at one end of the control rod near the distal end of the cannula for rotational and translational positioning relative thereto, the control rod including another end disposed near the proximal end of the cannula to facilitate manual rotational and translational manipulation of the dissection probe at said one end of the control rod in association with selective rotation of the cannula about an endoscope disposed within said lumen.

2. Surgical apparatus as in claim 1 wherein said distal end of the cannula includes a recess for enclosing the dissection probe therein in response to inward translational movement of the control rod relative to said distal end and in response to rotational alignment of (a) the cannula about an endoscope disposed within the lumen, and (b) the dissection probe rotatable with the control rod.

3. Surgical apparatus as in claim 2 including a fluid seal disposed within the recess about the control rod near the distal end of the cannula and disposed to receive an endoscope therethrough for maintaining fluid-tight engagement in response to relative movement of the endoscope and control rod relative to the fluid seal.

4. Surgical apparatus according to claim 2 including a fluid seal disposed near the proximal end of the cannula for receiving an endoscope therethrough to maintain fluid-tight engagement in response to relative movements of the endoscope.

5. Surgical apparatus according to claim 2 wherein the control rod and the dissection probe attached thereto translate relative to the cannula from within the recess at the distal end thereof to a location spaced forward of the distal end and within the viewing field of the endoscope.

6. Surgical apparatus as in claim 1 wherein an endoscope is positionable in substantially fixed axial position relative to the ends of the cannula.

7. Surgical apparatus according to claim 6 wherein an endoscope having a viewing end is positionable in fixed axial position relative to the cannula with the viewing end recessed within the cannula inwardly from the distal end thereof to exclude distal edges of the cannula from within a viewing field of the endoscope.

8. Surgical apparatus as in claim 1 wherein the dissection probe includes a substantial loop positioned in a plane skewed relative to the axis of the control rod.

9. Surgical apparatus comprising:

an elongated cannula having distal and proximal ends and including a first lumen therein between ends for rotatable receiving an endoscope therein; and a second lumen in the cannula eccentric of the first lumen between the ends of the cannula for supporting an instrument therein for rotational and translational manipulation thereof near the distal end of the cannula via controls near the proximal end of the cannula.

10. Surgical apparatus as in claim 9 including a fluid seal disposed within the second lumen near the distal end of the cannula to receive an instrument therethrough for maintaining fluid-tight engagement in response to relative movement of the instrument relative to the fluid seal.

11. Surgical apparatus as in claim 9 wherein the instrument within the second lumen includes an endoscope.

12. A method of endoscopic surgery with a cannula including a dissection probe positionable thereon and including a lumen for receiving an endoscope therein, the method comprising:

assembling an endoscope within the lumen of the cannula for rotation of the cannula relative to the endoscope at substantially fixed axial orientation relative to the cannula to provide visualization from a distal end of the cannula;

supporting the dissection probe on the cannula for rotation and translation relative thereto and in eccentric orientation relative to visualization through the endoscope, with the dissection probe near the distal end of the cannula;

inserting the distal end of the cannula within a surgical site; and selectively rotating the cannula relative to the endoscope received therein, and selectively rotating and translating the dissection probe relative to the cannula for selectively positioning the dissection probe within the surgical site in visualization through the endoscope.

13. A method of endoscopic surgery with a cannula including a first lumen for receiving an endoscope therein, and a second lumen for receiving therein an endoscopic instrument having an operative tip, the method comprising:

assembling an endoscope within the first lumen of the cannula for rotation of the cannula relative thereto at substantially fixed axial orientation relative to the cannula to provide visualization via the endoscope near a distal end of the cannula;

supporting the endoscopic instrument on the cannula for rotation and translation relative thereto and in eccentric orientation relative to visualization through the endoscope, with the operative tip of the endoscopic instrument near the distal end of the cannula;

inserting the distal end of the cannula within a surgical site; and selectively rotating the cannula relative to the endoscope received therein, and selectively rotating and translating the endoscopic instrument relative to the cannula for selectively positioning the endoscopic instrument within the surgical site in visualization through the endoscope.

14. Surgical apparatus as in claim 9 wherein the instrument within the second lumen includes an elongated rod with a dissection probe attached at an end thereof disposed near the distal end of the cannula.

* * * * *